(12) United States Patent
Heuser

(10) Patent No.: US 8,545,418 B2
(45) Date of Patent: Oct. 1, 2013

(54) SYSTEMS AND METHODS FOR ABLATION OF OCCLUSIONS WITHIN BLOOD VESSELS

(76) Inventor: Richard R. Heuser, Phoenix, AZ (US)

(*) Notice: Subject to any disclaimer, the term of this patent is extended or adjusted under 35 U.S.C. 154(b) by 761 days.

(21) Appl. No.: 12/356,446

(22) Filed: Jan. 20, 2009

(65) Prior Publication Data

US 2009/0125045 A1    May 14, 2009

Related U.S. Application Data

(63) Continuation-in-part of application No. 12/043,675, filed on Mar. 6, 2008, which is a continuation of application No. 10/927,340, filed on Aug. 25, 2004, now Pat. No. 7,402,141.

(51) Int. Cl.
*A61B 5/00* (2006.01)

(52) U.S. Cl.
USPC .......................................................... 600/585

(58) Field of Classification Search
USPC .................................. 600/585; 606/106, 159
See application file for complete search history.

(56) References Cited

U.S. PATENT DOCUMENTS

| | | |
|---|---|---|
| 2,729,211 A | 1/1956 | Peter |
| 3,751,305 A | 8/1973 | Huebscher |
| 3,788,318 A | 1/1974 | Kim et al. |
| 3,828,770 A | 8/1974 | Kuris et al. |
| 3,828,782 A | 8/1974 | Polin |
| 4,000,739 A | 1/1977 | Stevens |
| 4,241,289 A | 12/1980 | Bowling |
| 4,430,081 A | 2/1984 | Timmermans |
| 4,445,892 A | 5/1984 | Hussein et al. |
| 4,590,669 A | 5/1986 | Imamura |
| 4,630,609 A | 12/1986 | Chin |
| 4,634,342 A | 1/1987 | Rodewald |
| 4,634,432 A | 1/1987 | Kocak |
| 4,637,814 A | 1/1987 | Leiboff |
| 4,650,466 A | 3/1987 | Luther |
| 4,650,472 A | 3/1987 | Bates |

(Continued)

FOREIGN PATENT DOCUMENTS

| | | |
|---|---|---|
| EP | 0696447 | 2/1996 |
| EP | 0707864 | 4/1996 |

(Continued)

OTHER PUBLICATIONS

Baffour, M.S.C., R. et al. "An Angiographic Study of Ischemia as a determinant of Neovascularization in Arteriovenous Reversal." Surgery, Gynecology & Obstetrics. Jan. 1988. pp. 28-32. vol. 166.

(Continued)

*Primary Examiner* — Max Hindenburg
(74) *Attorney, Agent, or Firm* — Schwabe, Williamson & Wyatt P.C.

(57) ABSTRACT

Wire systems for the ablation of occlusions within blood vessels are provided. Systems include one or more wires configured for percutaneous insertion in a blood vessel, the wires configured to ablate an occlusion within the blood vessel. In some embodiments, a wire is gradually tapered near its distal end so that it can be used to pierce occlusions. In some cases, it may be used to dilate existing microchannels within occlusions. In some embodiments, a capture device is inserted towards the occlusion from either the same or opposite side as the tapered wire, and is used to draw the wire through the occlusion.

11 Claims, 12 Drawing Sheets

(56) References Cited

U.S. PATENT DOCUMENTS

| | | |
|---|---|---|
| 4,682,981 A | 7/1987 | Suzuki et al. |
| 4,705,511 A | 11/1987 | Kocak |
| 4,706,671 A | 11/1987 | Weinrib |
| 4,744,364 A | 5/1988 | Kensey |
| 4,771,777 A | 9/1988 | Horzewski et al. |
| 4,772,258 A | 9/1988 | Marangoni et al. |
| 4,796,640 A | 1/1989 | Webler |
| 4,832,688 A | 5/1989 | Sagae et al. |
| 4,862,891 A | 9/1989 | Smith |
| 4,874,378 A | 10/1989 | Hillstead |
| 4,883,460 A | 11/1989 | Zanetti |
| 4,895,564 A | 1/1990 | Farrell |
| 4,911,163 A | 3/1990 | Fina |
| 4,950,257 A | 8/1990 | Hibbs et al. |
| 4,994,071 A | 2/1991 | MacGregor |
| 5,078,684 A | 1/1992 | Yasuda |
| 5,092,846 A | 3/1992 | Nishijima et al. |
| 5,112,310 A | 5/1992 | Grobe |
| 5,147,336 A | 9/1992 | Wendell et al. |
| 5,163,906 A | 11/1992 | Ahmadi |
| 5,176,144 A | 1/1993 | Yoshikoshi et al. |
| 5,183,470 A | 2/1993 | Wettermann |
| 5,199,939 A | 4/1993 | Dake et al. |
| 5,207,228 A | 5/1993 | Roelandt et al. |
| 5,213,417 A | 5/1993 | Yamada et al. |
| 5,217,019 A | 6/1993 | Hughes |
| 5,217,484 A | 6/1993 | Marks |
| 5,234,437 A | 8/1993 | Sepetka |
| 5,242,410 A | 9/1993 | Melker |
| 5,256,141 A | 10/1993 | Gencheff et al. |
| 5,256,158 A | 10/1993 | Tolkoff et al. |
| 5,257,979 A | 11/1993 | Jagpal |
| 5,261,878 A | 11/1993 | Galindo |
| 5,267,966 A | 12/1993 | Paul |
| 5,275,488 A | 1/1994 | Stelts |
| 5,281,793 A | 1/1994 | Gavin et al. |
| 5,290,310 A | 3/1994 | Makower et al. |
| 5,292,311 A | 3/1994 | Cope |
| 5,320,617 A | 6/1994 | Leach |
| 5,330,486 A | 7/1994 | Wilk |
| 5,354,271 A | 10/1994 | Voda |
| 5,356,486 A | 10/1994 | Sugarman et al. |
| 5,364,392 A | 11/1994 | Warner et al. |
| 5,370,459 A | 12/1994 | Culbertson et al. |
| 5,380,304 A | 1/1995 | Parker |
| 5,395,341 A | 3/1995 | Slater |
| 5,399,088 A | 3/1995 | Mechley |
| 5,403,341 A | 4/1995 | Solar |
| 5,415,635 A | 5/1995 | Bagaoisan et al. |
| 5,423,774 A | 6/1995 | Fischell et al. |
| 5,437,292 A | 8/1995 | Kipshidze et al. |
| 5,439,446 A | 8/1995 | Barry |
| 5,443,478 A | 8/1995 | Purdy |
| 5,445,646 A | 8/1995 | Euteneuer et al. |
| 5,458,573 A | 10/1995 | Summers |
| 5,462,359 A | 10/1995 | Reichl et al. |
| 5,462,529 A | 10/1995 | Simpson et al. |
| 5,466,230 A | 11/1995 | Davila |
| 5,499,975 A | 3/1996 | Cope et al. |
| 5,512,291 A | 4/1996 | Li |
| 5,514,236 A | 5/1996 | Avellanet et al. |
| 5,545,193 A | 8/1996 | Fleischman et al. |
| 5,545,209 A | 8/1996 | Roberts et al. |
| 5,549,626 A | 8/1996 | Miller et al. |
| 5,578,008 A | 11/1996 | Hara |
| 5,591,137 A | 1/1997 | Stevens |
| 5,591,206 A | 1/1997 | Moufarrege |
| 5,599,325 A | 2/1997 | Ju et al. |
| 5,620,457 A | 4/1997 | Pinchasik et al. |
| 5,624,430 A * | 4/1997 | Eton et al. .................. 606/1 |
| 5,628,786 A | 5/1997 | Banas et al. |
| 5,632,760 A | 5/1997 | Sheiban et al. |
| 5,632,762 A | 5/1997 | Myler |
| 5,645,560 A | 7/1997 | Crocker et al. |
| 5,660,473 A | 8/1997 | Noma et al. |
| 5,665,107 A | 9/1997 | Hammerslag |
| 5,667,523 A | 9/1997 | Bynon et al. |
| 5,674,241 A | 10/1997 | Bley et al. |
| 5,681,295 A | 10/1997 | Gyure et al. |
| 5,683,453 A | 11/1997 | Palmaz |
| 5,688,266 A | 11/1997 | Edwards et al. |
| 5,695,498 A | 12/1997 | Tower |
| 5,707,359 A | 1/1998 | Bufalini |
| 5,725,524 A | 3/1998 | Mulier et al. |
| 5,725,572 A | 3/1998 | Lam et al. |
| 5,728,068 A | 3/1998 | Leone et al. |
| 5,733,044 A | 3/1998 | Rose et al. |
| 5,733,267 A | 3/1998 | Del Toro |
| 5,735,892 A | 4/1998 | Myers et al. |
| 5,743,900 A | 4/1998 | Hara |
| 5,749,880 A | 5/1998 | Banas et al. |
| 5,762,630 A | 6/1998 | Bley et al. |
| 5,769,077 A | 6/1998 | Lindegren |
| 5,792,070 A | 8/1998 | Kauphusman et al. |
| 5,800,393 A | 9/1998 | Sahota |
| 5,800,520 A | 9/1998 | Fogarty et al. |
| 5,807,350 A | 9/1998 | Diaz |
| 5,814,016 A | 9/1998 | Valley et al. |
| 5,814,064 A | 9/1998 | Daniel et al. |
| 5,820,607 A | 10/1998 | Tcholakian et al. |
| 5,830,222 A | 11/1998 | Makower |
| 5,830,224 A | 11/1998 | Cohn et al. |
| 5,833,644 A | 11/1998 | Zadno-Azizi et al. |
| 5,833,650 A | 11/1998 | Imran |
| 5,843,124 A | 12/1998 | Hammerslag |
| 5,843,166 A | 12/1998 | Lentz et al. |
| 5,853,409 A | 12/1998 | Swanson et al. |
| 5,855,563 A | 1/1999 | Kaplan et al. |
| 5,857,998 A | 1/1999 | Barry |
| 5,868,705 A | 2/1999 | Bagaoisan et al. |
| 5,868,708 A | 2/1999 | Hart et al. |
| 5,893,867 A | 4/1999 | Bagaoisan et al. |
| 5,897,497 A | 4/1999 | Fernandez |
| 5,897,819 A | 4/1999 | Miyata et al. |
| 5,899,917 A | 5/1999 | Edwards et al. |
| 5,906,636 A | 5/1999 | Casscells et al. |
| 5,910,364 A | 6/1999 | Miyata et al. |
| 5,911,710 A | 6/1999 | Barry et al. |
| 5,916,264 A | 6/1999 | Von Oepen |
| 5,928,260 A | 7/1999 | Chin et al. |
| 5,928,279 A | 7/1999 | Shannon et al. |
| 5,935,075 A | 8/1999 | Casscells et al. |
| 5,938,694 A | 8/1999 | Jaraczewski et al. |
| 5,944,019 A | 8/1999 | Knudson et al. |
| 5,957,961 A | 9/1999 | Maguire et al. |
| 5,964,798 A | 10/1999 | Imran |
| 5,968,064 A | 10/1999 | Selmon |
| 5,976,178 A | 11/1999 | Goldsteen et al. |
| 5,980,532 A | 11/1999 | Wang |
| 5,984,955 A | 11/1999 | Wisselink |
| 5,989,223 A | 11/1999 | Chu et al. |
| 6,004,310 A | 12/1999 | Bardsley et al. |
| 6,013,085 A | 1/2000 | Howard |
| 6,017,365 A | 1/2000 | Von Oepen |
| 6,019,779 A | 2/2000 | Thorud et al. |
| 6,022,336 A | 2/2000 | Zadno-Azizi et al. |
| 6,022,343 A | 2/2000 | Johnson et al. |
| 6,030,406 A | 2/2000 | Davis et al. |
| 6,033,434 A | 3/2000 | Borghi |
| 6,064,902 A | 5/2000 | Haissaguerre et al. |
| 6,068,656 A | 5/2000 | Von Oepen |
| 6,071,292 A | 6/2000 | Makower et al. |
| 6,120,534 A | 9/2000 | Ruiz |
| 6,124,523 A | 9/2000 | Banas et al. |
| 6,156,064 A | 12/2000 | Chouinard |
| 6,159,197 A | 12/2000 | Heuser |
| 6,168,579 B1 | 1/2001 | Tsugita |
| 6,176,872 B1 | 1/2001 | Miksza |
| 6,187,033 B1 | 2/2001 | Schmidtt et al. |
| 6,190,353 B1 | 2/2001 | Makower et al. |
| 6,193,747 B1 | 2/2001 | von Oepen |
| 6,231,587 B1 | 5/2001 | Makower |
| 6,245,052 B1 | 6/2001 | Orth et al. |
| 6,264,685 B1 | 7/2001 | Ahari |

| | | |
|---|---|---|
| 6,264,690 B1 | 7/2001 | Von Oepen |
| 6,283,958 B1 | 9/2001 | Vogl et al. |
| 6,308,090 B1 | 10/2001 | Tu et al. |
| 6,325,826 B1 | 12/2001 | Vardi et al. |
| 6,364,900 B1 | 4/2002 | Heuser |
| 6,383,214 B1 | 5/2002 | Banas et al. |
| 6,408,214 B1 | 6/2002 | Williams et al. |
| 6,464,665 B1 | 10/2002 | Heuser |
| 6,464,684 B1 | 10/2002 | Galdonik |
| 6,468,291 B2 | 10/2002 | Bates et al. |
| 6,475,226 B1 | 11/2002 | Belef et al. |
| 6,530,914 B1 | 3/2003 | Mickley |
| 6,536,949 B1 | 3/2003 | Heuser |
| 6,582,394 B1 | 6/2003 | Reiss et al. |
| 6,613,078 B1 | 9/2003 | Barone |
| 6,638,268 B2 | 10/2003 | Niazi |
| 6,648,837 B2 | 11/2003 | Kato et al. |
| 6,709,455 B1 | 3/2004 | Chouinard |
| 6,726,677 B1 | 4/2004 | Flaherty et al. |
| 6,746,479 B2 | 6/2004 | Ehr et al. |
| 6,830,568 B1 | 12/2004 | Kesten et al. |
| 6,858,038 B2 | 2/2005 | Heuser |
| 6,863,684 B2 | 3/2005 | Kim et al. |
| 6,866,805 B2 | 3/2005 | Hong et al. |
| 6,881,194 B2 | 4/2005 | Miyata et al. |
| 6,929,009 B2 | 8/2005 | Makower et al. |
| 6,987,660 B2 | 1/2006 | Stevenson et al. |
| 7,056,325 B1 | 6/2006 | Makower et al. |
| 7,059,330 B1 | 6/2006 | Makower et al. |
| 7,094,230 B2 | 8/2006 | Flaherty et al. |
| 7,134,438 B2 | 11/2006 | Makower et al. |
| 7,159,592 B1 | 1/2007 | Makower et al. |
| 7,166,088 B2 | 1/2007 | Heuser |
| 7,169,161 B2 | 1/2007 | Bonnette et al. |
| 7,179,250 B2 | 2/2007 | Heuser |
| 7,179,270 B2 | 2/2007 | Makower |
| 7,182,757 B2 | 2/2007 | Miyata et al. |
| 7,191,015 B2 | 3/2007 | Lamson et al. |
| 7,278,974 B2 | 10/2007 | Kato |
| 7,313,445 B2 | 12/2007 | McVenes et al. |
| 7,323,002 B2 | 1/2008 | Johnson et al. |
| 7,374,567 B2 | 5/2008 | Heuser |
| 7,402,141 B2 * | 7/2008 | Heuser .......................... 600/585 |
| 7,493,154 B2 * | 2/2009 | Bonner et al. ................. 600/424 |
| 7,918,859 B2 * | 4/2011 | Katoh et al. ................... 606/113 |
| 2001/0003161 A1 | 6/2001 | Vardi et al. |
| 2001/0049549 A1 | 12/2001 | Boylan et al. |
| 2002/0022858 A1 | 2/2002 | Demond et al. |
| 2002/0026211 A1 | 2/2002 | Khosravi et al. |
| 2002/0049467 A1 | 4/2002 | Gilson et al. |
| 2002/0161394 A1 | 10/2002 | Macoviak et al. |
| 2002/0178570 A1 | 12/2002 | Sogard et al. |
| 2003/0055402 A1 | 3/2003 | Zhou |
| 2003/0055484 A1 | 3/2003 | Lau et al. |
| 2003/0078614 A1 | 4/2003 | Salahieh et al. |
| 2003/0130598 A1 | 7/2003 | Manning et al. |
| 2003/0130684 A1 | 7/2003 | Brady et al. |
| 2003/0139797 A1 | 7/2003 | Johnson et al. |
| 2003/0163156 A1 | 8/2003 | Herbert et al. |
| 2003/0199967 A1 | 10/2003 | Hartley et al. |
| 2003/0212450 A1 | 11/2003 | Schlick |
| 2004/0019373 A1 | 1/2004 | Casey et al. |
| 2004/0082989 A1 | 4/2004 | Cook et al. |
| 2004/0098095 A1 | 5/2004 | Burnside et al. |
| 2004/0106978 A1 | 6/2004 | Greenberg et al. |
| 2004/0116831 A1 | 6/2004 | Vrba |
| 2004/0162603 A1 | 8/2004 | Golds et al. |
| 2004/0167607 A1 | 8/2004 | Frantzen |
| 2005/0080446 A1 | 4/2005 | Gilson et al. |
| 2005/0125011 A1 | 6/2005 | Spence et al. |
| 2006/0047222 A1 | 3/2006 | Heuser |
| 2006/0095070 A1 | 5/2006 | Gilson et al. |
| 2006/0217799 A1 | 9/2006 | Mailander et al. |
| 2006/0229638 A1 | 10/2006 | Abrams et al. |
| 2007/0021730 A1 | 1/2007 | Flaherty et al. |
| 2007/0073332 A1 | 3/2007 | Miller et al. |
| 2007/0083257 A1 | 4/2007 | Pal et al. |
| 2007/0162071 A1 | 7/2007 | Burkett et al. |
| 2007/0173878 A1 * | 7/2007 | Heuser .......................... 606/185 |
| 2008/0058860 A1 | 3/2008 | Demond et al. |
| 2008/0154153 A1 | 6/2008 | Heuser |

FOREIGN PATENT DOCUMENTS

| | | |
|---|---|---|
| EP | 0819411 | 1/1998 |
| EP | 0917886 | 5/1999 |
| EP | 1421970 | 5/2004 |
| FR | 2753907 | 3/1998 |
| JP | 0003094773 | 4/1991 |
| WO | 9214406 | 9/1992 |
| WO | 9640348 | 12/1996 |
| WO | 9717101 | 5/1997 |
| WO | 9800090 | 1/1998 |
| WO | 9811933 | 3/1998 |
| WO | 9819632 | 5/1998 |
| WO | 9826731 | 6/1998 |
| WO | 9839047 | 9/1998 |
| WO | 9908744 | 2/1999 |
| WO | 9913808 | 3/1999 |
| WO | 9924105 | 5/1999 |
| WO | 9934749 | 7/1999 |
| WO | 9936002 | 7/1999 |
| WO | 0166038 | 3/2001 |
| WO | 2005096995 | 10/2005 |

OTHER PUBLICATIONS

Bernheim, M.D., Bertram. "Arteriovenous Anastomosis—Reversal of the Circulation—As a Preventative of Gangrene of the Extremeties." Arteriovenous Anastomosis. Undated.

Blaisdell, M.D., William, et al. "Revascularization of Severely Ischemic Extremeties with an Arteriovenous Fistula." American Journal of Surgery. Aug. 1966. pp. 166-174. vol. 112.

Cuttino Jr., John, et al. "Collateral Vessel Formation: Isolation of a Transferrable Factor Promoting a Vascular Response." Basic Research in Cardiology. Jan. 9, 1975. pp. 568-573. vol. 70, No. 5.

Elsner, M.D., Mathias, et al. "Coronary Stent Grafts Covered by a Polytetrafluoroethylene Membrane." The American Journal of Cardiology. Aug. 1, 1999. pp. 335-338. vol. 84.

Gerard, M.D., Dava et al. "Acute Physiologic Effects of Arteriovenous Anastomosis and Fistual in Revascularizing the Ischemic Canine Hind Limb." Surgery. Apr. 1981. pp. 485-493. vol. 89, No. 4.

Goldsmith, M.D., Harry et al. "Lipid Angiogenic Factor from Omentum." JAMA. Oct. 19, 1984. pp. 2034-2036. vol. 252, No. 15.

Halstead, M.D., Albert. "Arteriovenous Anastomosis in the Treatment of Gangrene in the Extremeties." Surgery, Gynecology and Obstetrics. 1912. pp. 1-19. vol. 16.

Heuser, M.D., Richard R., et al. "Endoluminal Grafting for Percutaneous Aneurysm Exclusion in an Aortocoronary Saphenous Vein Graft: The First Clinical Experience." Journal of Endovascular Surgery. 1995. pp. 81-88. vol. 2.

Howell, M.D., Marcus, et al. "Preliminary Results of Endovascular Abdominal Aortic Aneurysm Exclusion with the AneuRx Stent-Graft." Journal of the American College of Cardiology. 2001. pp. 1040-1048. vol. 38, No. 4.

Johnson & Johnson Gateway, LLC. "Chronic Total Occlusion (CTO) Technologies."http://www.jnjgateway.com/home.jhtml?loc= USENG&page=viewContent&contentId=09008b9881163810& parentId=09008b988163810. 2007. Printed Jan. 17, 2007.

Kalmar, M.D., Gabor, et al. "Radial Force and Wall Apposition of Balloon-expandable Vascular Stent in Eccentric Stenoses: An In Vitro Evaluation in a Curved Vessel Model." Journal of Vascular and Interventional Radiology. May 2002. pp. 499-508. vol. 13, No. 5.

Kumar, S. et al. "Angiogenesis Factor from Human Myocardial Infarcts." The Lancet. Aug. 13, 1983. pp. 364-368.

Matolo, M.D., Nathaniel. "Use of an Arteriovenous Fistula for Treatment of the Severely Ischemic Extremity: Experimental Evaluation." Ann. Surg. Nov. 1976. pp. 622-625. vol. 184, No. 5.

Oesterle, et al. "An Embolization Containment Device." Catheterization and Cardiovascular Interventions. 1999. pp. 243-250. vol. 47.

Robertson, M.D., Roy, et al. "Collateral Circulation in the Presence of Experimental Arteriovenous Fistula." Surgery. Jan. 1950. pp. 1-16. vol. 27, No. 1.

Root, M.D., Harlan, et al. "Effects of an Arteriovenous Fistula on the Devascularized Limb." JAMA. Feb. 22, 1965. pp. 109-112. vol. 191, No. 8.

Rossi, Anne V. "510(k) Summary per 21 CFR 807.92 re BCS IQ Hydrophilic Guide Wire and Response Letter from Department of Health and Human Services." Aug. 1, 2003.

Sheil, A.G.R. "Treatment of Critical Ischaemia of the Lower Limb by Venous Arterialization: An Interim Report." Br. J. Surg. 1977. pp. 1997-199.

Szilagyi, M.D., Emerick. "Femoral Arteriovenous Anastomosis in the Treatment of Occlusive Arterial Disease." A.M.A. Archives of Surgery. Undated.

Terumo Medical Corporation. "Glidewire Hydrophilic Coated Guidewire Designed for Peripheral Applications." http://terumomedical.com/SubDepts.asp?myID=79. 2002. Printed Jan. 30, 2007.

* cited by examiner

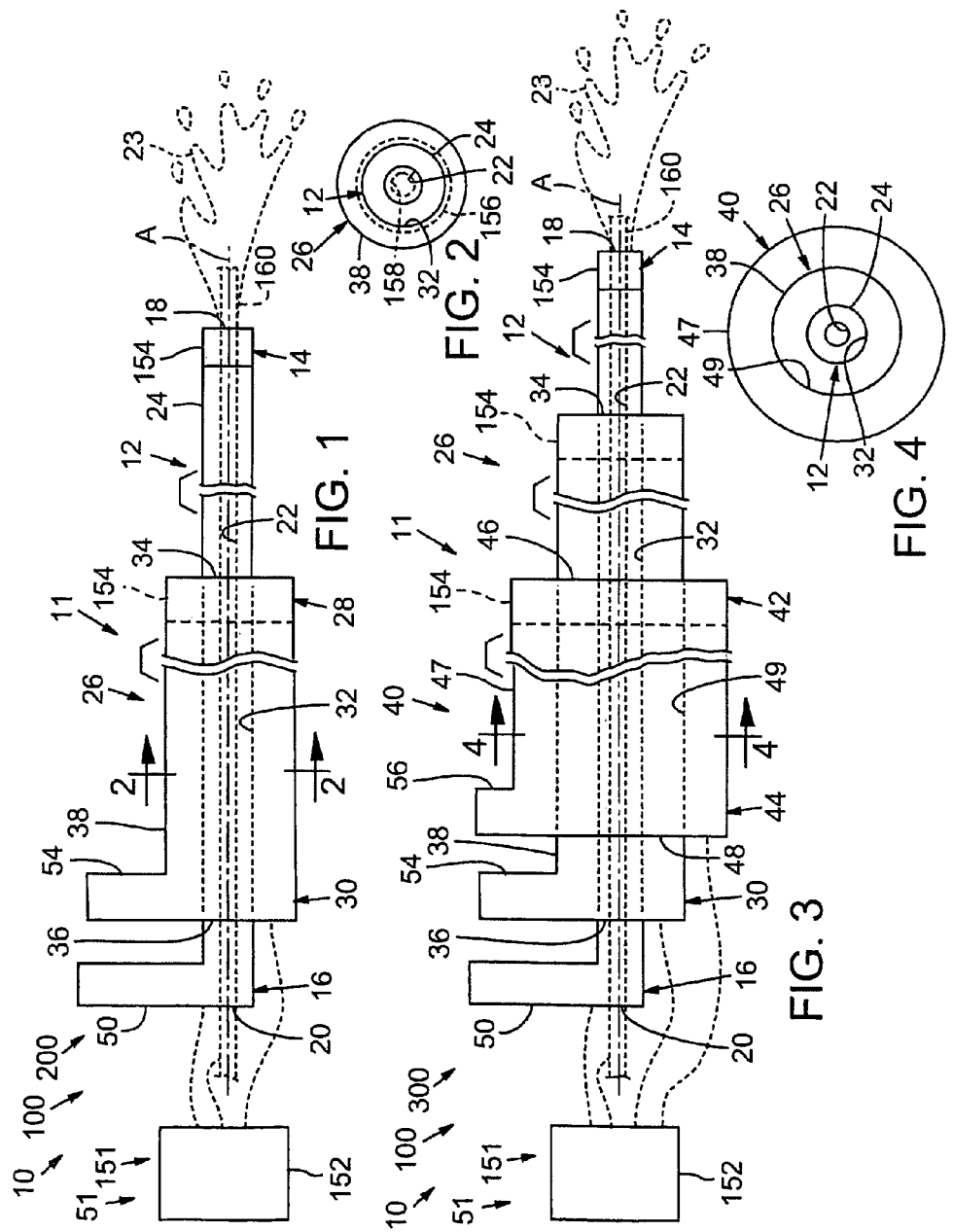

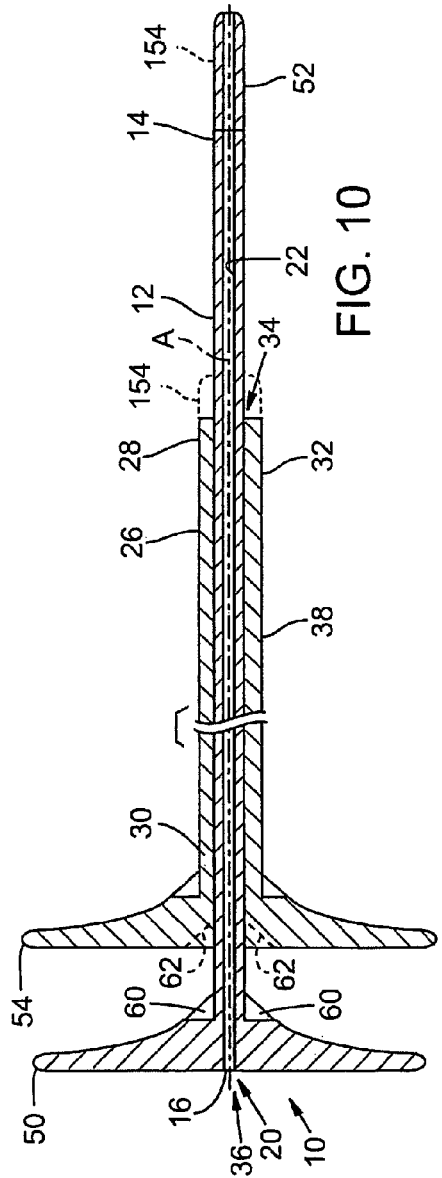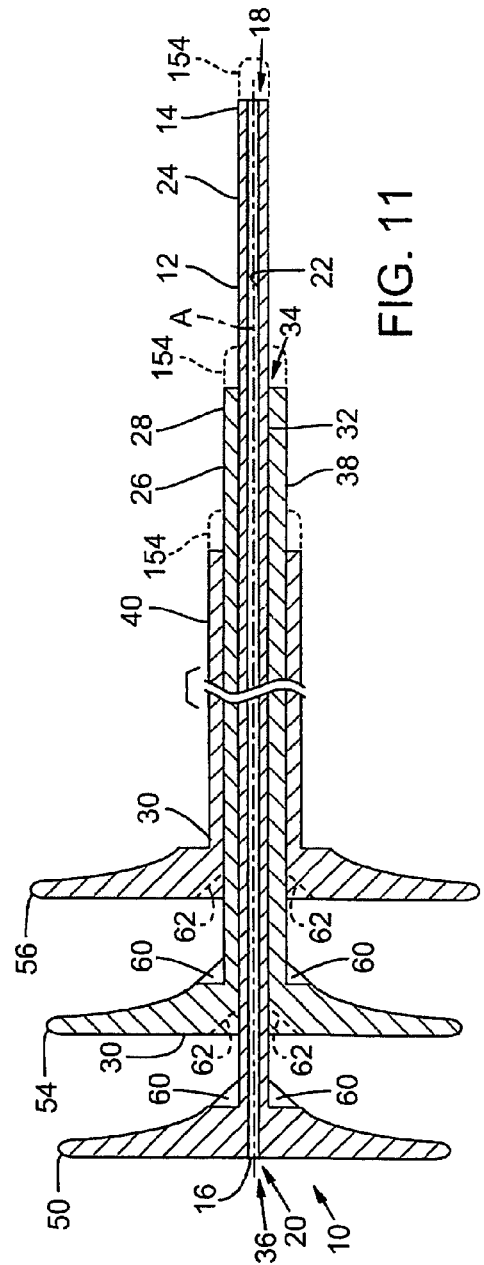

SYSTEMS AND METHODS FOR ABLATION OF OCCLUSIONS WITHIN BLOOD VESSELS

RELATED APPLICATIONS

This application is a continuation-in-part of, and claims benefit under 35 U.S.C. § 120 to, U.S. patent application Ser. No. 12/043,675, entitled "MULTIPLE-WIRE SYSTEMS AND METHODS FOR ABLATION OF OCCLUSIONS WITHIN BLOOD VESSELS," filed on Mar. 6, 2008, which is a continuation-in-part of U.S. patent application Ser. No. 10/927,340, entitled "CATHETER GUIDEWIRE SYSTEM USING CONCENTRIC WIRES," filed on Aug. 25, 2004 and issued as U.S. Pat. No. 7,402,141 on Jul. 22, 2008, the content of which is hereby incorporated by reference for all purposes.

SUMMARY

Multiple-wire systems for the ablation of occlusions within blood vessels according to the present disclosure may include two or more concentric wires configured for percutaneous insertion in a blood vessel. Some embodiments further include a radio-frequency device configured to deliver radio-frequency energy to one or more of the concentric wires. Some embodiments include one or more concentric wires having a textured outer surface that aids in the passage of the wire through a blood vessel.

Methods according to the present disclosure for ablating an occlusion within a blood vessel may include percutaneously inserting two or more concentric wires into a blood vessel, feeding the concentric wires through the blood vessels, manipulating one or more of the concentric wires to engage the occlusion, and applying radio-frequency energy to a distal end of one or more of the concentric wires to ablate the occlusion.

BRIEF DESCRIPTION OF THE DRAWINGS

FIG. 1 is a schematic illustration of multiple-wire systems according to the present disclosure that include two concentric wires.

FIG. 2 is a schematic cross-sectional illustration of the systems of FIG. 1 taken along line 2-2.

FIG. 3 is a schematic illustration of multiple-wire systems according to the present disclosure that include three concentric wires.

FIG. 4 is a schematic cross-sectional illustration of the systems of FIG. 3 taken along line 4-4.

FIG. 10 is a cross-sectional side view of a multiple-wire system according to the present disclosure, the system including two concentric wires, each wire including a handle.

FIG. 11 is a cross-sectional side view of a multiple-wire system according to the present disclosure, the system including three concentric wires, each wire including a handle.

DETAILED DESCRIPTION

Figure 5:
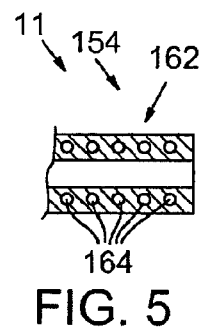
FIG. 5 is a schematic cross-sectional illustration of a wire tip of a multiple-wire system according to the present disclosure, the wire tip including a portion of a radio-frequency device therein.

In a first aspect, multiple-wire systems are schematically illustrated in FIGS. 1-4 and are generally indicated at 10. Systems 10 may include two or more concentric wires 11. Wires 11 may additionally or alternatively be described as guidewires. Wires 11 may (but are not required to) be constructed at least partially with a hydrophilic material (e.g., coated with a polytetrafluoroethylene (PTFE) or plastic covering) selected for a particular procedure being performed. As used herein, the term 'hydrophilic' refers to a property of a material where the material becomes slippery when subjected to a fluid, such as a liquid. Accordingly, wires 11 made of a hydrophilic material may be less likely to snag within a blood vessel or to accidentally poke through the wall of a blood vessel, such as when the wire is being routed around a bend or turn of a vessel.

Multiple wire systems may (but are not required to) further include a treatment device 51 in the form of a radio-frequency device 151 operatively connected to one or more of wires 11. Such embodiments that include a radio-frequency device 151 may be referred to as radio-frequency, or RF, wire systems 100. Additionally or alternatively, systems 10 may include a treatment device 51 that incorporates a laser energy device, an optical coherent reflectometry (OCR) device, an ultrasound device, or any other device suitable for mounting on a wire or catheter and for controlling from outside the body while inserted in the body.

A wire 11 may have a generally cylindrical outer surface that defines an outer diameter. Additionally or alternatively, a wire 11 may have an outer surface that generally tapers at least partially along its overall length. For example, a wire may have a greater diameter at its proximal end than at its distal end. Such a wire may have a proximal end diameter equal to about 0.061 cm (0.024 inches) and a distal end diameter equal to about 0.025 cm (0.01 inches); however, other configurations are equally within the scope of the present disclosure. Additionally or alternatively, a wire may have a generally cylindrical outer surface for a portion of its length and a tapered outer surface for another portion of its length. Other configurations are equally within the scope of the present disclosure, and the schematic illustrations of FIGS. 1-4 are not to be interpreted as limiting wires 11 to having only cylindrical outer surfaces with constant outer diameters.

An example of a two-wire system is schematically illustrated in FIGS. 1 and 2, and an example of a three-wire system is schematically illustrated in FIGS. 3 and 4. Systems with more than three wires are equally within the scope of the present disclosure.

In the non-exclusive example illustrated in FIG. 1, an RF system 100 including two concentric wires is generally indicated at 200. System 200 includes a first, inner wire 12, a second wire 26 through which first wire 12 extends, and a radio-frequency device 151 operatively connected to one or both of the first and second wires.

First wire 12 includes a distal end 14 and a proximal end 16, and has a length that may be selected for a particular type of procedure to be conducted in a human blood vessel. For example, first wire 12 may be between about 150 cm and about 300 cm; however, other lengths are equally within the scope of the present disclosure. Inner wire 12 may (but is not required to) include an opening 18 adjacent distal end 14, an opening 20 adjacent proximal end 16, and a central lumen 22 extending between the proximal and distal openings, which may define an inner diameter of first wire 12.

Embodiments that include a lumen 22 within first wire 12 may be used to deliver a fluid 23 (including liquids and gases), such as (but not Limited to) water, saline, compressed air or other gas, pharmaceuticals (whether in liquid or gas form), etc., to a site within a blood vessel. For example, a delivered fluid may be used to break up an occlusion and/or to expand an already partially open occlusion. In such embodiments, lumen 22 may (but is not required to) be coated with a fluid-impervious coating to prevent the migration of fluid 23 through the wall of first wire 12 when a system is used to deliver a fluid to a site within a blood vessel.

First wire 12 may (but is not required to) have a generally cylindrical outer surface 24 defining an outer diameter, which may be between about 0.010 cm (0.004 inches) and about 0.036 cm (0.014 inches), or may be larger or smaller as selected for a particular procedure and for compatibility with other wires, catheters, sheaths, and other equipment. Alternatively, as mentioned, first wire 12 may have an outer surface 24 that tapers at least partially along its length.

Additionally or alternatively, first wire 12 may include an outer surface 24 that has a textured surface that is configured to provide a mechanism for aiding with the insertion and/or passage of wire 12 through a blood vessel in response to an operator manipulating the wire (e.g., by twisting it), as discussed in more detail below in reference to FIG. 8.

Inner wire 12 may be provided with a handle portion 50 adjacent proximal end 16 that a user (e.g., a physician) may use in manipulating the wire about and along a central axis A of the wire. Handle portion 50 may (but is not required to) be removable in some embodiments. Wire 12 may be constructed with a hydrophilic material (e.g., coated with a Teflon or plastic covering) selected for a particular procedure being performed.

Second wire 26 may be constructed to be deployed over first wire 12. Additionally or alternatively, second wire 26 may be described as being constructed to receive first wire 12, such that first wire 12 is deployed within second wire 26 after second wire 26 has already been deployed within a blood vessel.

Second wire 26 includes a distal end 28 and a proximal end 30, and has a length that is compatible with first wire 12, for example, less than the length of first wire 12. The length of second wire 26 may be selected for a particular type of procedure to be conducted in a human blood vessel. For example, the length may be between about 125 cm and about 275 cm; however, other lengths are equally within the scope of the present disclosure. Second wire 26 includes an opening 34 adjacent distal end 28, an opening 36 adjacent proximal end 30, and a central lumen 32 extending between the distal and proximal openings, which may define an inner diameter of second wire 26. The inner diameter is sized so as to receive and permit first wire 12 to extend therethrough and permit relative movement between the first and second wires. In some embodiments, though not required, central lumen 32 of second wire 26 may be configured to compliment the outer surface 24 of inner first wire 12. For example, in embodiments where the outer surface of the first inner wire is configured with a textured surface, the central lumen of the second wire may (but is not required to) be configured with a corresponding textured inner surface that is adapted to compliment the textured outer surface of the inner wire, as discussed in more detail below in reference to FIG. 8.

Second wire 26 may have a generally cylindrical outer surface 38 defining an outer diameter, which may be between about 0.052 cm (0.008 inches) and about 0.089 cm (0.035 inches), or may be larger or smaller as selected for a particular procedure and for compatibility with other wires, catheters, sheaths, and other equipment. Alternatively, as mentioned, second wire 26 may have an outer surface 38 that tapers at least partially along its length.

Additionally or alternatively, second wire 26 may include a textured outer surface that is configured to provide a mechanism for aiding with the insertion and/or passage of wire 26 through a blood vessel in response to an operator manipulating the wire (e.g., by twisting it), as discussed in more detail below in reference to FIG. 8.

Second wire 26 may be provided with a handle portion 54 adjacent proximal end 30 that a physician may use in manipulating the wire about and along central axis A. Handle portion 54 may (but is not required to) be removable in some embodiments.

Second wire 26 may (but is not required to) have a rigidity selected to be greater than that of first wire 12, thus providing the system with an overall variable rigidity which depends on the extent to which the first wire extends out of the second wire.

One or more of wires 11 may (but are not required to) be constructed in sections. In such embodiments the wire(s) may be constructed without transitions between the sections. For example, wires 11 may be used in crossing a bifurcation in the blood vessel, and may be provided with a rigidity selected to allow the bifurcation crossing. Rigidity may be controlled by the use of braiding or the selection of various materials. For example, nitinol is flexible, but it becomes stiffer as more stainless steel is added.

As mentioned, RF wire systems 100 may include an RF device 151. Such devices may include an RF-generating device 152 operatively connected to one or more of wires 11 and configured to generate radio-frequency energy that may be delivered to at least a portion of one or more of wires 11. For example, as illustrated in FIG. 1, RF-generating device 152 may deliver RF energy to first wire 12. Additionally or alternatively, RF-generating device 152 may deliver RF energy to second wire 26. Examples of RF-generating devices and RF devices in general are disclosed in U.S. Pat. Nos. 6,190,379, 6,485,489, and 7,229,469, and U.S. patent application Ser. Nos. 11/433,198 and 11/688,785, the contents of which are hereby incorporated by reference for all purposes. Additional examples of RF-generating devices and RF devices in general include the Boa System™, the Boa-Surg Device™, and the Boa-Cathe Device™ offered by QuantumCor, Inc. of San Clemente, Calif. and the Safe-Cross® RF Crossing Wire device offered by IntraLuminal Therapeutics, Inc. of Carlsbad, Calif. Such devices may be used with, or adapted for use with, systems 100 according to the present disclosure to provide the RF energy that may be delivered to one or more of wires 11.

In some embodiments of RF wire systems 100, one or more of wires 11 may include an RF-delivery tip 154 positioned at the distal end thereof. Such delivery tips may be configured to receive RF energy from RF-generating device 152 and deliver the RF energy to an occlusion, for example, or other blockage or structure to be ablated during a procedure. Various configurations of delivery tips are within the scope of the present disclosure and are discussed in more detail below. Delivery tips 154 may be described as comprising a portion of an RF device 151.

The RF energy may be routed to the RF delivery tip(s) in any number of ways that may be appropriate for a specific configuration of system 100. For example, the bulk of a wire 11 (e.g., the conductive portions thereof) may be charged with the RF energy. Alternatively, the RF energy may be delivered solely to a tip portion via a wire or other structure that is generally insulated from the bulk of the wire 11 to which a specific tip 154 is being charged.

In embodiments where the bulk of a wire 11 is charged with RF energy, the given wire may be coated with an insulative covering to avoid transfer of the RF energy to an adjacent concentric wire 11, for example, as schematically illustrated in FIG. 2 at 156 as coating the outer surface 24 of first wire 12. Additionally or alternatively, the lumen of a given wire 11 may be coated with an insulative lining, for example, as schematically illustrated in FIG. 2 at 158 as coating the central lumen 22 of first wire 12. Other configurations are equally within the scope of the present disclosure. A non-exclusive example of an insulative material that may be used in such embodiment is polytetrafluoroethylene (PTFE).

In embodiments where first wire 12 includes a central lumen 22, systems 10 according to the present disclosure may (but are not required to) further include a mandril 160 configured to extend through first wire 12. Mandril 160 may be considered a wire 11 according to the present disclosure; however, mandril 160 may or may not include a central lumen, and may generally be a cylindrical wire adapted to provide treatment or diagnostic abilities for systems 10. For example, mandril 160 may be charged with RF energy for the ablation of an occlusion or other tissue. Examples of mandrils 160 are disclosed in U.S. Pat. No. 6,190,379, incorporated above.

FIGS. 3 and 4 schematically illustrate an example of a three-wire RF wire system 300. Like systems 200, systems 300 include a first wire 12, a second wire 26 through which first wire 12 extends, and a radio-frequency device 151. A third wire 40 is also provided that may be constructed to be deployed over second wire 26. Additionally or alternatively, third wire 40 may be described as being constructed to receive second wire 26, such that second wire 26 is deployed within third wire 40 after third wire 40 has already been deployed within a blood vessel.

Third wire 40 includes a distal end 42 and a proximal end 44, and has a length that is compatible with first and second wires 12, 26, for example less than that of second wire 26. The length of third wire 40 may be selected for a particular type of procedure to be conducted in a human blood vessel. For example, the length may be between about 100 cm and 250 cm; however, other lengths are equally within the scope of the present disclosure. Third wire 40 includes an opening 46 adjacent distal end 42, an opening 48 adjacent proximal end 44, and a central lumen 49 extending between the proximal and distal openings, which may define an inner diameter of third wire 40. The inner diameter is sized so as to receive and permit second wire 26 to extend therethrough and permit relative movement between the second and third wires. In some embodiments, though not required, central lumen 49 of third wire 40 may be configured to compliment the outer surface 38 of second wire 26. For example, in embodiments where the outer surface of the second wire is configured with a textured surface, the central lumen of the third wire may (but is not required to) be configured with a corresponding textured inner surface that is adapted to compliment the textured outer surface of the second wire, as discussed in more detail below in reference to FIG. 8.

Third wire 40 may have a generally cylindrical outer surface 47 defining an outer diameter, which may be between about 0.025 cm (0.010 inches) and about 0.089 cm (0.035 inches), or may be larger or smaller as selected for a particular procedure and for compatibility with other wires, catheters, sheaths, and other equipment. Alternatively, as mentioned, third wire 50 may have an outer surface 47 that tapers along at least a portion of its length.

Additionally or alternatively, third wire 40 may include a textured outer surface that is configured to provide a mechanism for aiding with the insertion and/or passage of third wire 40 through a blood vessel in response to a user manipulating the wire (e.g., by twisting it), as discussed in more detail below in reference to FIG. 8.

Third wire 40 may be provided with a handle portion 56 adjacent proximal end 44 that a physician may use in manipulating the wire about and along central axis A. Handle portion 56 may (but is not required to) be removable in some embodiments.

Third wire 40 may (but is not required to) have a rigidity selected to be greater than that of the first and second wires, thus providing the system with an overall variable rigidity that depends on the extent to which the second wire extends out of the third wire, and the extend to which the first wire extends out of the second wire.

Figure 6:
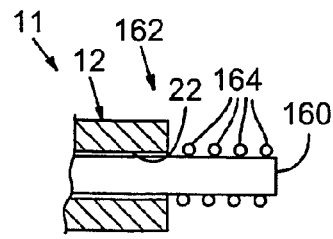
FIG. 6 is a schematic cross-sectional illustration of a wire tip of a multiple-wire system according to the present disclosure, the wire tip having a mandril extending therethrough and a portion of a radio-frequency device mounted on the distal end of the mandril.
Figure 7:
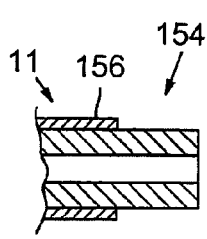
FIG. 7 is a schematic cross-sectional illustration of a portion of a wire of a multiple-wire system according to the present disclosure, the wire including an insulative coating and an exposed tip.

As mentioned, one or more of wires 11 may include an RF-delivery tip 154 positioned at the distal end thereof. Non-exclusive examples of delivery tips 154 are illustrated in FIGS. 5-7. In the embodiment illustrated in FIG. 5, wire 11 includes an RF energy collection structure 162 in the form of a plurality of spaced apart rings 164 embedded within tip 154.

Additionally or alternatively, collection structure 162 may take the form of a coil. Rings 164, or similarly a coil, may be configured to absorb RF energy delivered to tip 154 by an associated RF-generating device through the bulk of wire 11 or through an associated wire or other structure that is generally insulated from the bulk of wire 11. A non-exclusive example of a material that may be appropriate for the construction of rings 164, or a coil, is gold. Other configurations of RF energy collection and delivery structure are equally within the scope of the present disclosure and may be incorporated into systems 10.

FIG. 6 illustrates a non-exclusive example of a system 10 that includes a mandril 160 extending through a first wire 12. In such an embodiment, rather than energizing the distal end of the first wire 12 with radio-frequency energy, the distal end of the mandril may include radio-frequency energy collection structure 162 in the form of a plurality of spaced apart rings 164, or in the form of a coil, wrapped around the distal end of the mandril.

FIG. 7 illustrates yet another non-exclusive example of a delivery tip 154. In this embodiment, rather than including RF energy collection structure, the wire 11 includes an insulative covering 156 as discussed above, with the covering leaving at least a portion of the distal end of wire 11 exposed. In such an embodiment, the entire wire 11, or at least the bulk of wire 11, may be charged with RF energy, while only the distal end is exposed within a blood vessel when being used, and therefore may be used to ablate an occlusion or other tissue therein.

As discussed above, wires 11 of systems 10 may (but are not required to) include textured outer surfaces configured to provide a mechanism for aiding with the insertion of a wire through a blood vessel, or occlusion therein, in response to an operator manipulating the wire. For example, one or more of the outer surfaces may have a spiraled, screw-like, or threaded configuration that aids with the insertion and/or passage of a wire through a blood vessel in response to an operator twisting the wire 11. For example, a wire 11 may be formed by a plurality of wound or braided wires or wire strands. A non-exclusive example of a system 10 including such structure is illustrated in FIG. 8.

Figure 8:
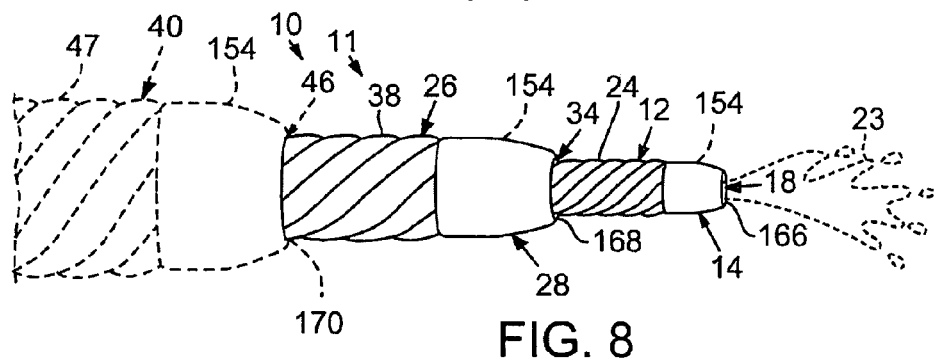
FIG. 8 is an isometric side view of a portion of a multiple-wire system according to the present disclosure, the system including wires that include a plurality of wound wire strands.

In the illustrated non-exclusive embodiment of FIG. 8, a system 10 includes a first wire 12 and a second wire 26, constructed of a plurality of smaller wires wound about their respective lumens. Accordingly, outer surface 24 of first wire 12 and outer surface 38 of second wire 26 provide a screw-like or threaded configuration. As illustrated in dashed lines, systems 10 having wires 11 with textured outer surfaces are not limited to two-wire systems, and may further include a third wire 40. Additional wires beyond three are equally within the scope of the present disclosure.

Additionally, though not required, in embodiments where an outer wire (i.e., a second, third, or further wire having a concentric wire extending therethrough) includes a textured configuration as discussed, the central lumen of the outer wire may be configured with a corresponding textured inner surface (e.g., in the form of female threads, or the like) that is adapted to compliment the textured outer surface of the inner wire, and thereby provide for relative screw-like displacement of the inner wire within the outer wire when a user twists the inner wire within the outer wire.

Multiple-wire systems having wires 11 with textured outer surfaces and an inner wire with a central lumen may be particularly well suited for the delivery of a fluid to a site within a blood vessel. By having a plurality of concentric wires, the fluid may be generally prevented from leaking through the structure that defines the textured outer surface. For example, in embodiments where the textured outer surface of a wire is defined by a plurality of wound or braided wire strands, depending on the fluid being used for a particular procedure, the fluid may tend to leak through the wound or braided wire strands. By having one or more outer wires, fluid that manages to leak through the structure of the inner wire may generally be contained by the outer one or more wires. Additionally or alternatively, the central lumen of the inner wire may be lined with a coating (e.g., polytetrafluoroethylene (PTFE), plastic, or other suitable material) to generally prevent migration of the fluid through the wall of the inner wire. Additionally or alternatively, a tube (e.g., constructed of PTFE, plastic, or other suitable material) may be positioned within the central lumen of one or more of the concentric wires.

Additionally, though not required, embodiments that include wires with textured surfaces may include RF-delivery tips 154 for the delivery of RF energy within a blood vessel.

Additionally or alternatively, in some embodiments the distal openings to wires 11 may be defined by a cutting edge configured to aid in the passage of wires 11 through blood vessels and through occlusions, other blockages, or tissue therein. For example, in the non-exclusive embodiment illustrated in FIG. 8, distal opening 18 of first wire 12 may be defined by a cutting edge 166, distal opening 34 of second wire 26 may be defined by a cutting edge 168, and distal opening 46 of third wire 40 may be defined by a cutting edge 170. Such cutting edges may simply be thinner than the thickness of the rest of the wire 11, or alternatively may be defined by serrations or other structure configured to aid in the cutting through an occlusion, blockage, or other tissue. Such configurations may be particularly useful in embodiments that include a textured outer surface of a wire 11, as discussed above. Accordingly, as a user inserts a wire 11 through a blood vessel and reaches an occlusion or other blockage within a blood vessel, the user may twist the wire causing the distal opening to cut through the blockage and thereby facilitate further insertion of the wire, with or without the addition of RF energy.

Figure 9:
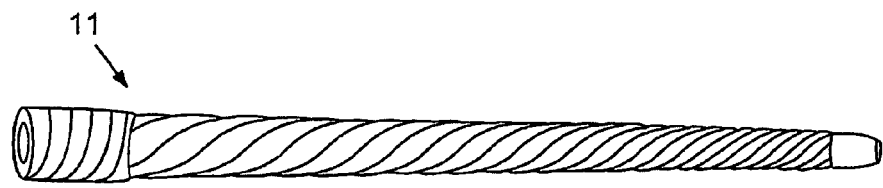
FIG. 9 is an isometric side view of a wire according to the present disclosure, the wire tapered and including a plurality of wound wire strands.

Wires 11 according to the present disclosure are not limited to being cylindrical, and as discussed above and illustrated in FIG. 9, may have portions that are generally tapered or cone-shaped. The non-exclusive example illustrated in FIG. 9 further includes a textured outer surface, although other configurations of tapered wires, including wire having smooth outer surfaces, are equally within the scope of the present disclosure.

Further non-exclusive examples of systems 10 according to the present disclosure may be described as below in reference to FIGS. 10 and 11.

As shown in FIGS. 10 and 11, embodiments of guidewire systems of the present disclosure are multiple-wire systems indicated generally at 10. Systems 10 may include an inner wire 12 having a distal end 14 and a proximal end 16. Inner wire 12 has a length that may be selected for a particular type of procedure to be conducted in a human blood vessel, e.q., between about 180 cm and about 300 cm. Inner wire 12 may include an opening 18 adjacent distal end 14 and an opening 20 adjacent proximal end 16, and a central lumen 22 extending between the proximal and distal openings. Central lumen 22 defines an inner diameter for wire 12, and wire 12 also has a generally cylindrical outer surface 24 defining an outer diameter. The outer diameter of inner wire 12 may be between about 0.010 cm (0.004 inches) and about 0.036 cm (0.014 inches), and my be any size therebetween, or larger or smaller as selected for the desired procedure and for campatibility with other wires, catheters, sheaths, and other equipment.

Inner wire 12 may be provided with a handle 50, preferably (but not required to be) removable, adjacent proximal end 16 that a physician may use in manipulating the wire about and along a central axis A of the wire. Wire 12 is may be constructed with a hydrophilic material selected for the particular procedure. For example, coating with a polytetrafluoroethylene (PTFE) or plastic covering makes a wire hydrophilic.

Wire 12 may be constructed without transitions between sections, if it includes any sections, of the wire. Inner wire 12 may be used in crossing a bifurcation in a blood vessel, and may be provided with a rigidity selected to allow the bifurcation crossing. Rigidity may be controlled by the use of braiding or the selection of various materials. For example, nitinol is flexible, but it becomes stiffer as more stainless steel is added.

As best seen in FIG. 10, inner wire 12 may optionally include a treatment or a diagnostic device 52 (e.g., in the form of an RF-delivery tip 154 as discussed above), typically Located at the distal end 14 of wire 12. Alternatively, device 52 may be located in a more proximal position on wire 12, or may be located on the other wires or catheter to be described below. Device 52 may be any type of device useful for treating or diagnosing conditions in blood vessels, such as a radio-frequency energy device, a laser energy device, an optical coherent reflectometry (OCR) device, an ultrasound device, or any other device suitable for mounting on a wire or catheter and for controlling from outside the body while inserted in the body.

A second wire 26, preferably constructed to be deployed over inner wire 12, includes a distal end 28 and a proximal end 30 and a length preferably selected to be compatible with inner wire 12. A central lumen 32 of wire 26 extends between a distal opening 34 and a proximal opening 36. As mentioned, second wire 26 may include an RF-delivery tip 154 at its distal end.

Central lumen 32 of second wire 26 defines an inner diameter for the wire. Wire 26 may have a generally cylindrical outer surface 38 defining an outer diameter. The outer diameter of wire 26 may be between about 0.020 cm (0.008) inches and about 0.089 cm (0.035 inches), and may be any size therebeween, or larger or smaller as selected for the desired procedure and for compatibility with other wires, catheters, sheaths, and other equipment.

Wire 26 may be provided with a handle 54, preferably (but not required to be) removable, adjacent proximal end 30 that the physician may use in manipulating the wire about and along a central axis A of the wire. Second wire 26 may have a rigidity selected to be greater than that of inner wire 12, thus providing the system with an overall variable rigidity which depends on the extent to which the inner wire extends out of the second wire.

System 10 may also include a third or outer wire 40, as shown in FIG. 11, having proximal and distal ends with openings and a central lumen communicating therebetween, inner and outer diameters, and a generally cylindrical outer surface as for the other wires. Preferably third wire 40 is sized to fit over the second wire and includes a handle 56, preferably (but not required to be) removable, coupled adjacent the proximal end for manipulation of the third wire about and along central axis A. Third wire 40 may have a rigidity selected to be greater than the rigidity of the first wire and greater than the rigidity of the second wire, thus providing the system with an overall variable rigidity which depends on the extent to which the inner wire extends out of the second wire, and the extent to which the second wire extends out of the third wire. Third wire 40 may also include an RF-delivery tip 154 at its distal end.

Third wire 40 may have an outer diameter between about 0.025 cm (0.010 inches) and about 0.089 cm (0.035 inches), and may be any size therebetween, or larger or smaller as selected for the desired procedure and for compatibility with other wires, catheters, sheaths, and other equipment. Typically, the length of the third wire is less than the length of the second wire, and the length of the second wire is less than that of the inner wire.

Figure 13:
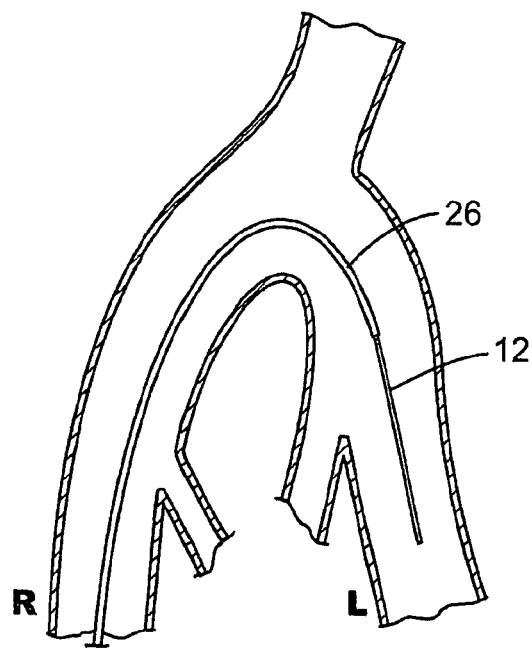
FIG. 13 is a cross-sectional view, from a perspective of facing the patient, of contralateral access by a multiple-wire system according to the present disclosure from the right iliac artery to the left iliac artery.

The multiple guidewire system may be combined with a catheter, such as catheter 58 that can be inserted over the wires, as shown in FIG. 13. Such a catheter may include a balloon and a stent placement apparatus. As described above, the catheter or one or more of the wires may be provided with a radio-frequency energy device, a laser energy device, and/or an optical reflectometry device for applying treatment within the blood vessel, or with other devices, including diagnostic devices such as ultrasound.

When the first, second, and third wires are coupled together, any of the handles of the first, second, and third wires may be used to manipulate all three wires, and also the wires may be manipulated relative to one another by simultaneous use of two or three of the handles. For example, as shown in FIGS. 10 and 11, handles 50 and 54 may include one or more forward-facing wings 60, which interlock with corresponding notches 62 in handles 54 and 56, when the handles are pushed together. When the wings and notches interlock, rotational movement of one handle will also rotate the Wire attached to the interlocked handle. Alternatively, any other type of selective interlocking may be used, or the friction between the wires may provide for simultaneous movement, unless the handles are separately manipulated.

The length of the first wire may be between about 180 cm and about 300 cm, but may be other sizes as desired for particular procedures. The length of the second wire may be about 5 cm less than the first wire, and the length of the third wire may be about 5 cm less than the second wire.

Figures 12A, 12B:
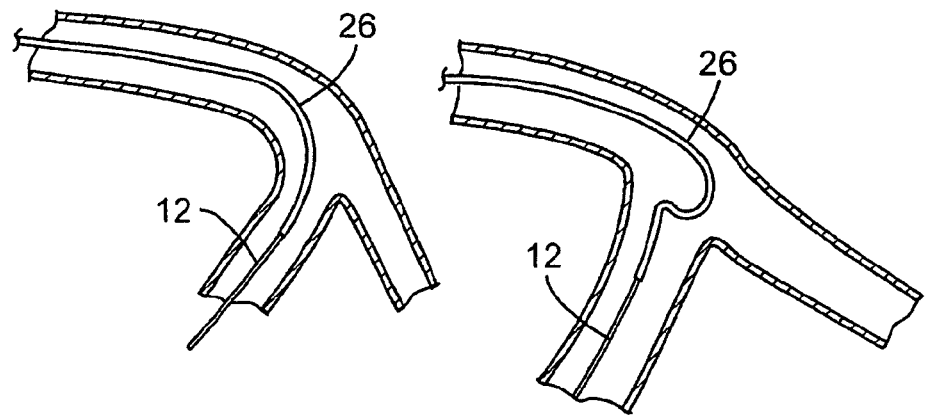
FIGS. 12A and 12B are cross-sectional views of two wires of a multiple-wire system according to the present disclosure, the wires extending around a bend adjacent a bifurcation in a human blood vessel, showing the difference in performance between a transitionless wire (12A) and a wire with a transition (12B).

FIGS. 12A and 12B show two examples of a two-guidewire system, including inner wire 12 and outer wire 26, being used to extend around a bend and into one channel at a bifurcation in a human blood vessel. FIG. 12A shows the performance of a transitionless wire, which can extend around the corner without doubling over, while FIG. 12B shows the performance of a wire with a transition, which tends to double over. The transition typically occurs where two materials that are different in hydrophilicity or stiffness are directly joined, and a transitionless wire is typically provided by gradually changing the hydrophilicity or stiffness, or by other methods of preventing the abrupt transition.

Figure 14:
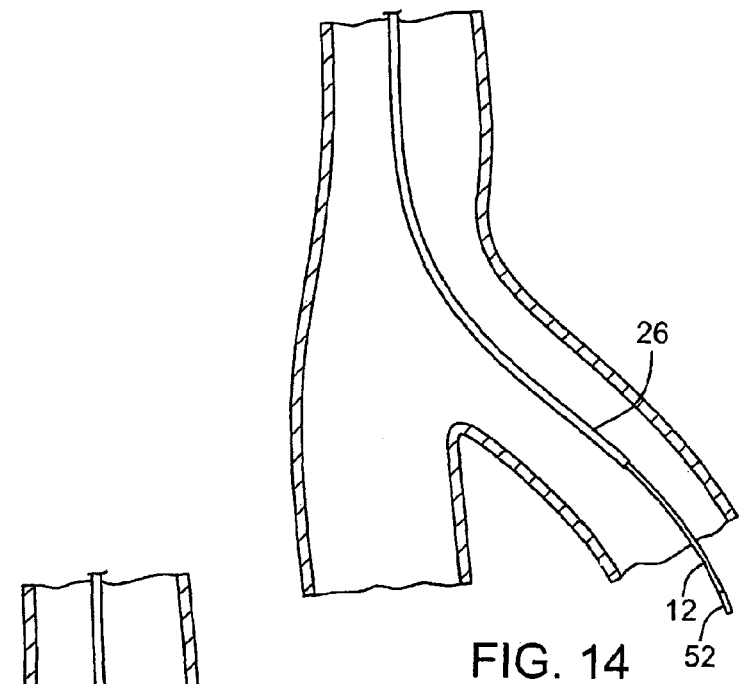
FIG. 14 is a cross-sectional view of a two-wire system according to the present disclosure being maneuvered into a branch of a blood vessel.
Figure 15:
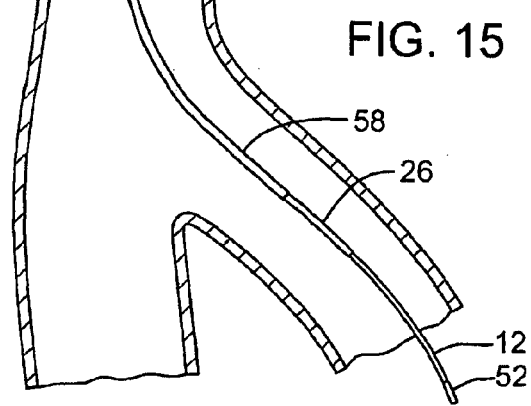
FIG. 15 is a cross-sectional view of a two-wire system according to the present disclosure with a catheter being maneuvered into a branch of a blood vessel.

FIG. 13 shows contralateral access by the guidewire system from the right iliac artery R to the left iliac artery L. FIG. 14 shows a two-wire guidewire system, including inner wire 12 and outer wire 26, and treatment/diagnostic device 52, being maneuvered into a branch of a blood vessel. FIG. 15 shows the two-wire guidewire system with catheter 58 being maneuvered into a branch of a blood vessel.

Figure 16:
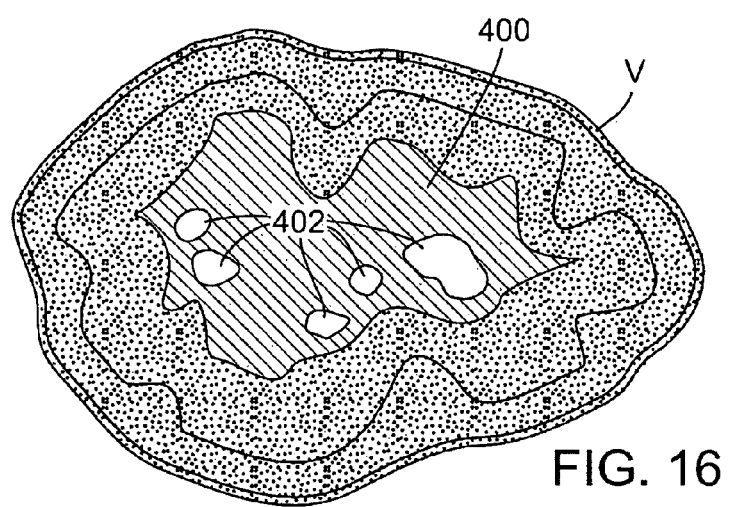
FIG. 16 is a cross-sectional view of a chronic total occlusion within a blood vessel that includes a plurality of microchannels.

Another aspect involves utilization of a single wire and possibly a capture device, as well as exploiting existing characteristics of a chronic total occlusion ("CTO"), in order to obtain access to an area of a blood vessel distal the CTO. FIG. 16 depicts a cross-sectional view of a CTO 400 in a blood vessel V. CTO 400 includes one or more microchannels 402 that may be expanded to gain access through CTO 400. For example, microchannel 402 may be expanded to form a channel through CTO 400 into which a needle or other instrument can be inserted. Devices and methods for performing such a procedure utilizing various occlusion-penetrating devices are depicted in FIGS. 17-23. For reference, CTO 400 has a proximal surface 404 and an opposite distal surface 406 (see, e.g., FIGS. 19A and B).

Figure 17:
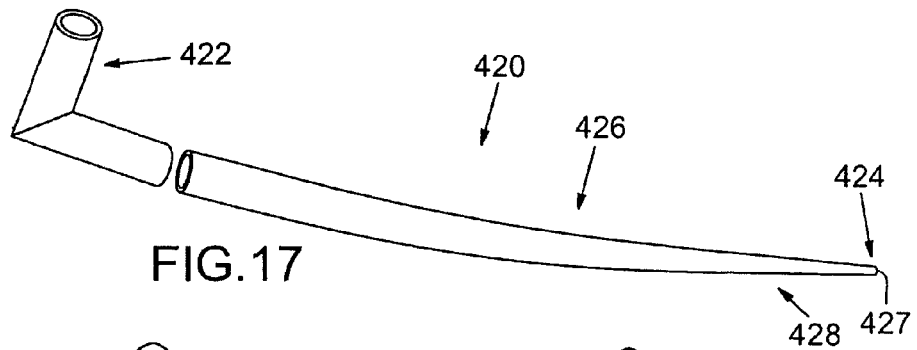
FIG. 17 depicts a tapered wire, similar to the one shown in FIG. 9 except without a textured surface.
Figures 19A, 19B:
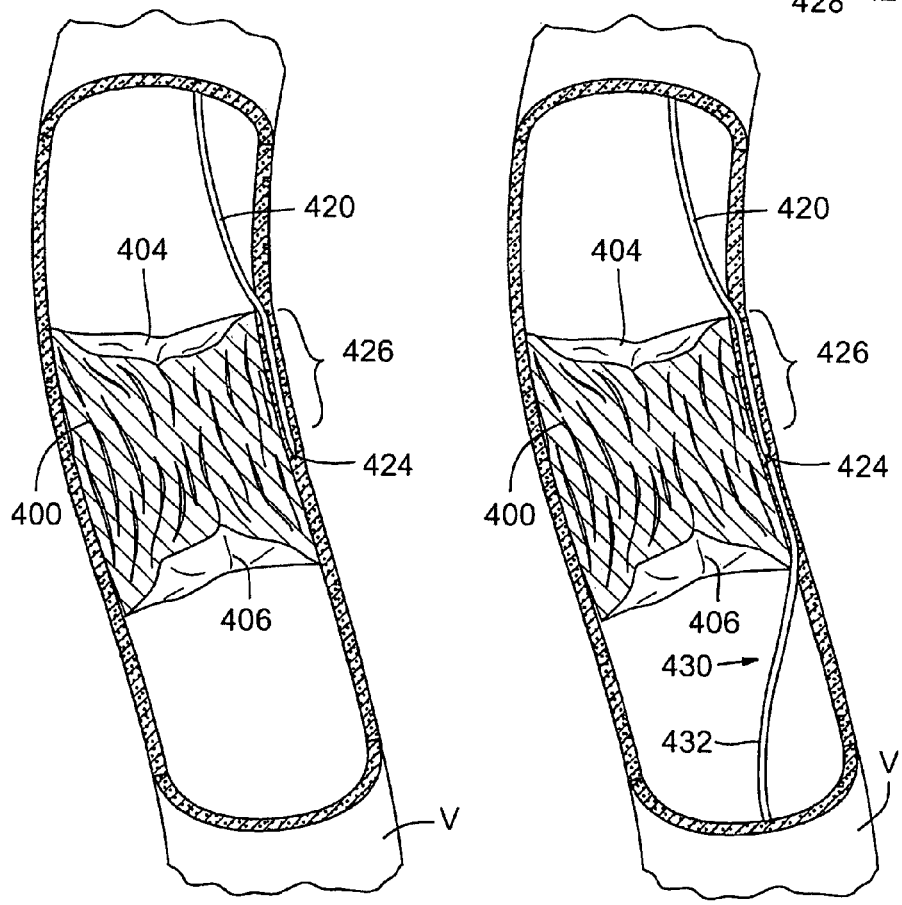
FIGS. 19A-B depict a method of using a first wire and a capture device to traverse a chronic total occlusion.

FIG. 17 depicts an example apparatus including a first wire 420 having a proximal end 422 operable by a physician, a distal end 424 and a gradually tapered portion 426 adjacent distal end 424. Gradually tapered portion 426 terminates at a sharp tip 427 at distal end 424. As will be more fully understood from the discussion below, first wire 420 may include a first magnet 428.

First wire 420 may be a wire that is incorporated into one of the multiple-wire systems described above. For example, wire 420 may be the same as inner wire 12 shown in FIGS. 1 and 3. Accordingly, first wire 420 may include a radio-frequency device 151 and RF-delivery tip 154 adjacent its distal end 424 for breaking apart at least a portion of CTO 400 (see FIGS. 1, 3, 5, 7 and 8).

Figure 18A:
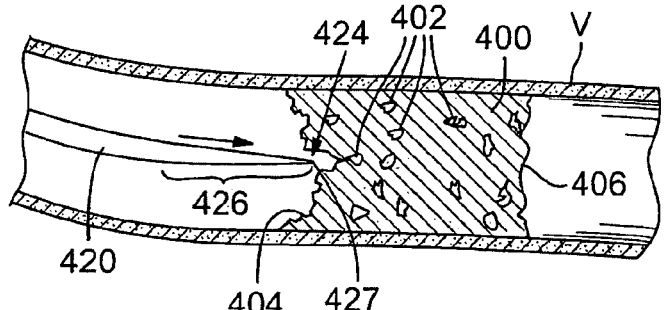
FIGS. 18A-C depict a method of using a first wire having a tapered portion to gradually dilate a microchannel of a chronic total occlusion.
Figure 18B:
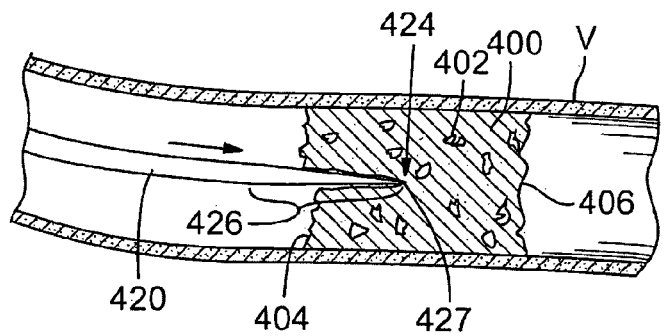
Figure 18C:
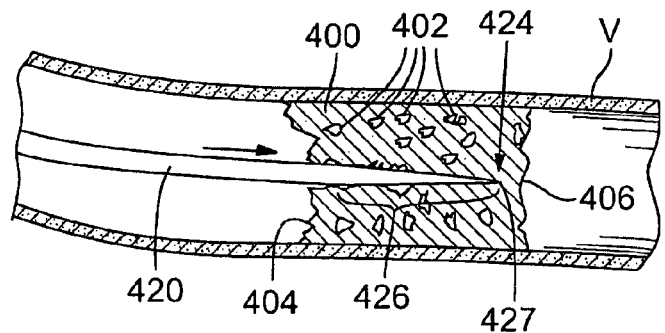

A particularly effective method of penetrating an occlusion is depicted in FIGS. 18A-C. As shown in FIG. 18A, first wire 420 is inserted into the blood vessel V to a position where distal tip 424 of first wire 420 is adjacent a microchannel 402 of CTO 400. First wire 420 is then advanced towards CTO 400 so that gradually tapered portion 426 gradually dilates microchannel 402 (FIGS. 18B and C) and eventually gains access through CTO 400.

First wire 420 may be inserted at least partially or all of the way through occlusions in blood vessels in ways other than directly through CTO 400. For example, in FIG. 19A, first wire 420 traverses CTO 400 in vessel V via the subintimal space in the vessel wall adjacent CTO 400. First wire 420 may also be inserted directly into an occlusion (e.g., into a microchannel 402), or through the space between the side of an occlusion and the wall of the blood vessel V.

It may be difficult to obtain complete access through an occlusion using only first wire 420. In such cases, a capture device 430 may be deployed to draw distal end 424 of first wire 420 through CTO 400. For example, in FIG. 19B, capture device 430 includes a second wire 432 that is inserted from the opposite side of CTO 400 as first wire 420 towards distal surface 406 so that second wire 432 can be used to draw distal end 424 of first wire 420 to a position distal of distal surface 406 of CTO 400.

Figure 20A:
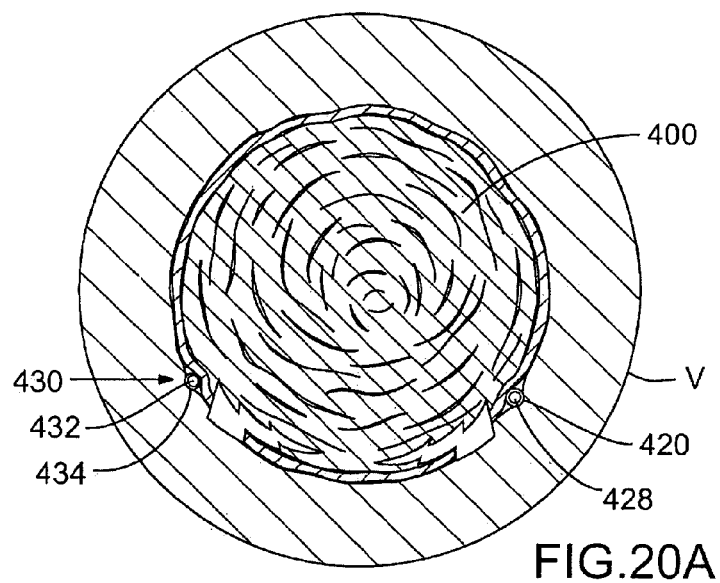
FIGS. 20A-B are cross-sectional views of the vessel being treated using a method similar to that depicted in FIGS. 19A-B.
Figure 20B:
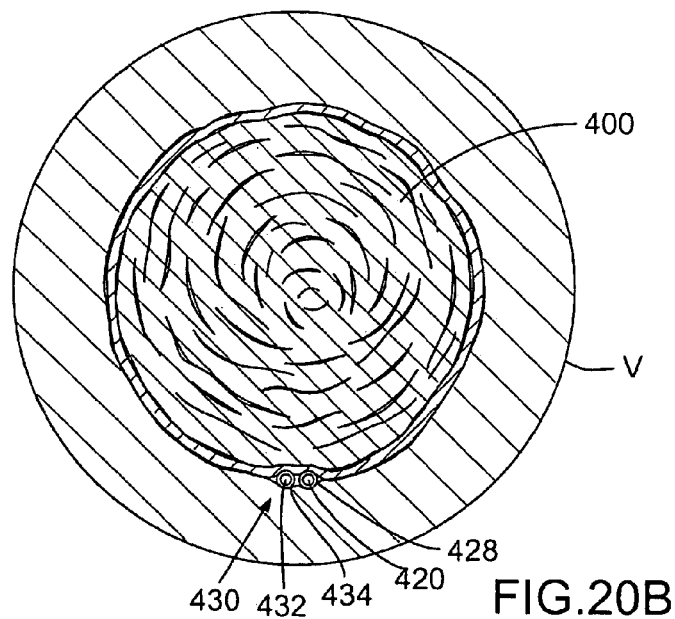
Figure 21:
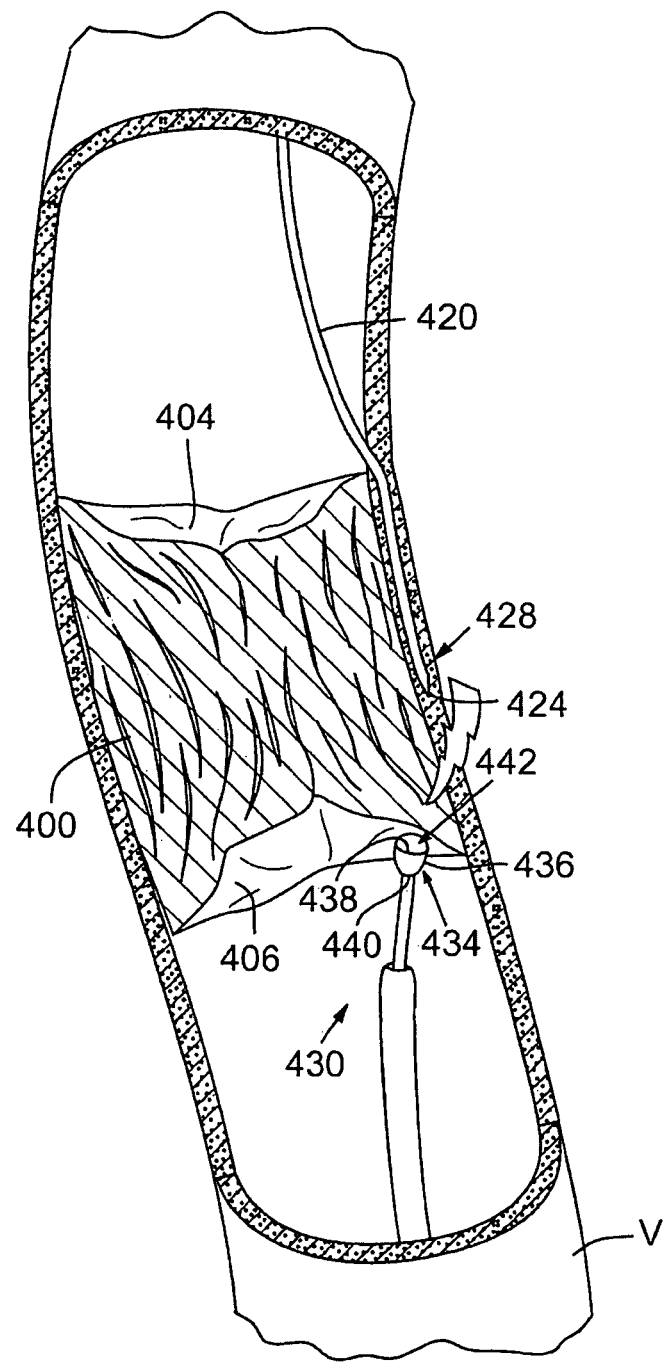
FIG. 21 depicts another method of using a first wire and a capture device with a receptor to traverse a chronic total occlusion.

In some embodiments, first wire 420 and/or second wire 432 include a first magnet 428 and/or a second magnet 434. Each of these magnets may be adapted to attract, or possibly repel, the other magnet. Referring now to FIGS. 20A and B, which depict cross sectional views of the vessel being treated in FIG. 19A, first wire 420 and second wire 432 are inserted into the subintimal space of blood vessel V. However, the wires are at different points of the circumference of the vessel wall. To bring the wires together, first wire 420 includes first magnet 428 and second wire 432 includes second magnet 434, and the magnets are operated to draw first wire 420 and second wire 432 together, as shown in FIG. 20B. It should be understood that the reference numerals 420, 428, 432 and 434 are point at the first and second wires generally, and not to any particular portion of the wires (because, for example, the magnets 428 and 434 can be at various positions near the distal tips of the wires, or the distal tips themselves may be magnetic).

In some embodiments, capture device 430 includes other features for capturing and/or drawing first wire 420 through an occlusion. For example, in FIG. 21, capture device 430 includes a receptor 436 for receiving distal end 424 of first wire 420. Receptor 436 includes a distal opening 438, a proximal end 440 and a channel 442 therebetween. In some embodiments, channel 442 may be tapered in a direction from distal opening 438 to proximal end 440. In some embodiments, such as the one shown in FIG. 21, receptor 436 includes a magnet 434 adapted to attract distal end 424 (which may contain a magnet 428) of first wire 420 along channel 442 towards proximal end 440. Such a receptor is described in U.S. Pat. No. 7,374,567 to Heuser, the disclosure of which is incorporated by reference for all purposes.

Figure 22A:
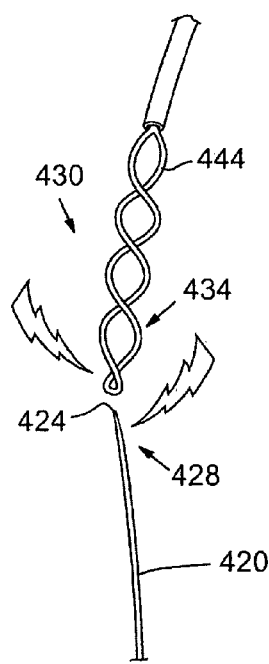
FIGS. 22A-B depict another method of using a first wire and a retractable-loop snare to traverse a chronic total occlusion.
Figure 22B:
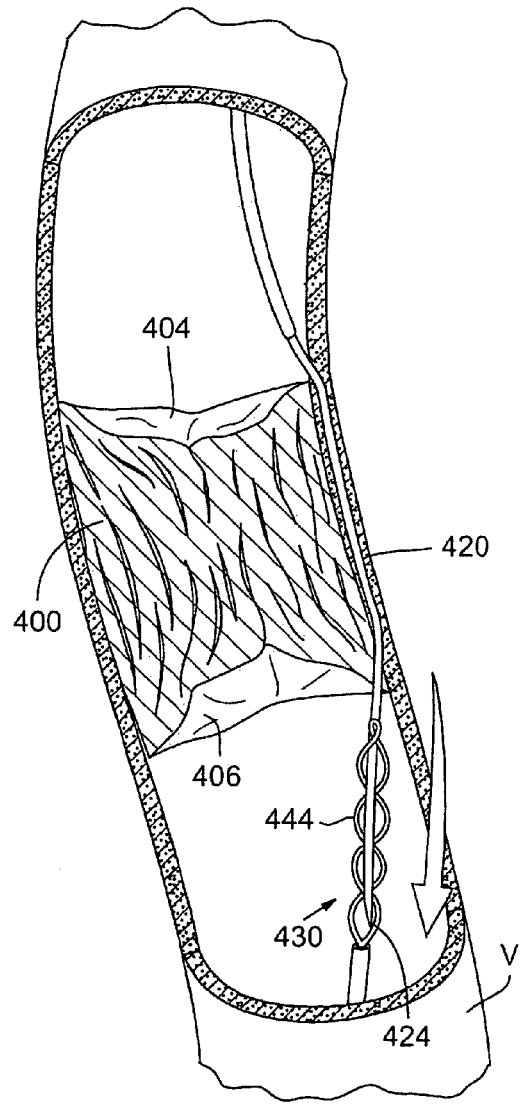

FIGS. 22A and B depict another embodiment of capture device 430 comprising a retractable loop snare 444. FIG. 22A depicts first wire 420 and retractable loop snare 444 outside of a living body and in close proximity. In this example, first wire 420 and retractable loop snare 444 include first magnet 428 and second magnet 434, respectively, but it should be understood that magnets are not required. Retractable loop snares suitable for the methods described herein are described in U.S. Pat. No. 6,554,842 to Heuser, the disclosure of which is incorporated by reference herein for all purposes. FIG. 22B depicts first wire 420 being captured by retractable loop snare 444 and drawn through the subintimal space proximate CTO 400.

In the examples discussed above, first wire 420 and capture device 430 are advanced towards CTO 400 from opposite directions. However, this is not required, and as will be described below, first wire 420 and capture device 430 may be inserted into vessel V towards CTO 400 from the same direction.

Figures 23A, 23B:
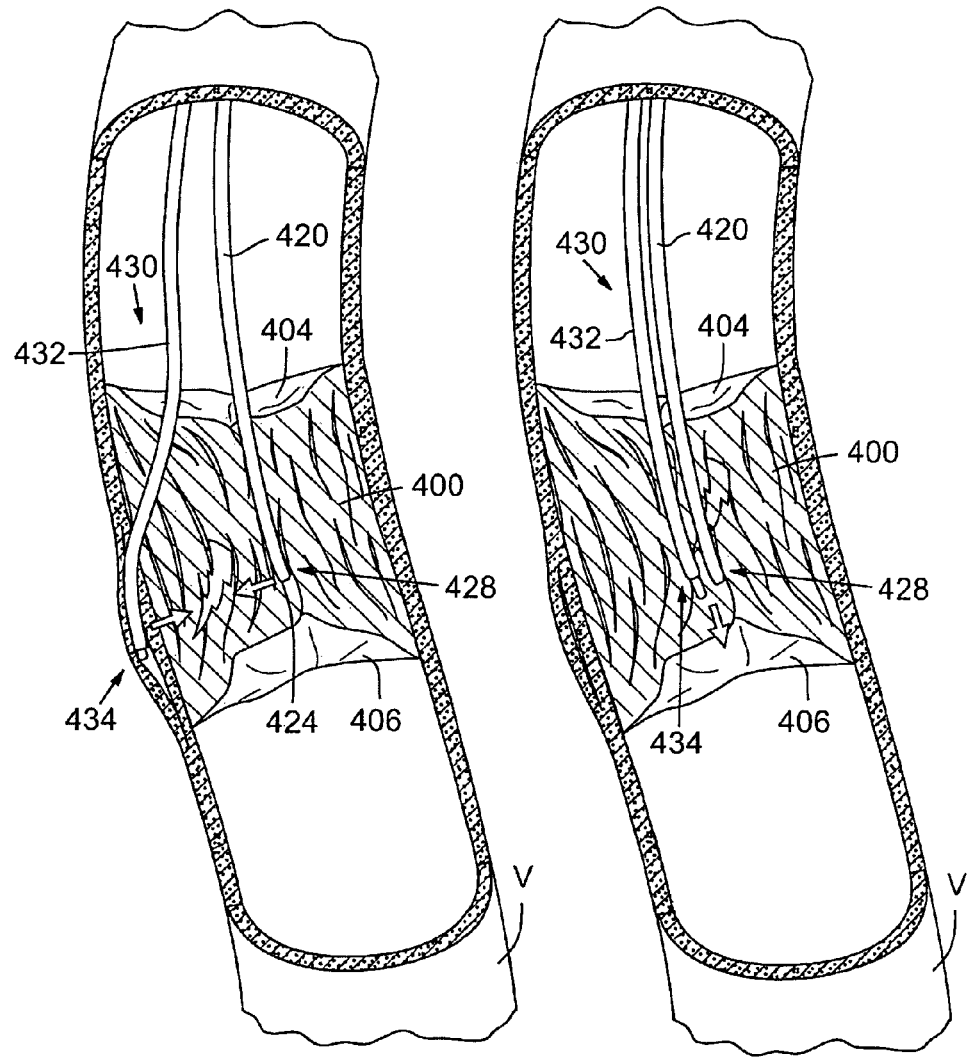
FIGS. 23A-B depict another method of using a first wire and a capture device inserted from the same direction as the first wire to traverse a chronic total occlusion.

Referring now to FIG. 23A, first wire 420 is inserted partially through CTO 400 and capture device 430, in the form of second wire 432, is inserted into subintimal space adjacent CTO 400. First wire 420 and second wire 432 include first magnet 428 and second magnet 434, respectively, so that first wire 420 and second wire 432 are attracted towards one another. This magnetic attraction is utilized to draw the wires together through CTO 400 in the directions indicated by the arrows in FIG. 23A, which may also break up a portion of CTO 400. As a result, the wires will be immediately adjacent, as shown in FIG. 23B.

The disclosure set forth above encompasses multiple distinct embodiments with independent utility. While each of these embodiments has been disclosed in a preferred form or method, the specific alternatives, embodiments, and/or methods thereof as disclosed and illustrated herein are not to be considered in a limiting sense, as numerous variations are possible. The present disclosure includes all novel and non-obvious combinations and subcombinations of the various elements, features, functions, properties, methods and/or steps disclosed herein. Similarly, where any disclosure above or claim below recites "a" or "a first" element, step of a method, or the equivalent thereof, such disclosure or claim should be understood to include one or more such elements or steps, neither requiring nor excluding two or more such elements or steps.

Various combinations and subcombinations of features, functions, elements, properties, steps and/or methods may be claimed through presentation of new claims in a related application. Such new claims, whether different, broader, narrower, or equal in scope to the original claims, are also regarded as included within the subject matter of the present disclosure.

What is claimed is:

1. A multiple-wire system for obtaining access through an occlusion within a blood vessel, comprising:
   a first wire configured for percutaneous insertion in the blood vessel towards a proximal surface of the occlusion, the first wire comprising:
   a first outer wire having a proximal end, a distal end, and a generally cylindrical outer surface, wherein the first outer wire includes an opening adjacent the distal end, an opening adjacent the proximal end, and a central lumen communicating therebetween;

a first middle wire configured for insertion in the blood vessel through the central lumen of the outer wire, the first middle wire having a proximal end, a distal end and a generally cylindrical outer surface, wherein the first middle wire includes an opening adjacent the distal end, an opening adjacent the proximal end, and a central lumen communicating therebetween, wherein the first middle wire is longer than the first outer wire; and a first inner wire having a proximal end, a distal end, and a gradually tapered portion adjacent the distal end, wherein the first inner wire gradually tapered portion is configured to penetrate and pass through the occlusion, and wherein the gradually tapered portion comprises a first magnet having a diameter no greater than the gradually tapered portion; and a capture device configured for percutaneous insertion in the blood vessel towards a distal surface of the occlusion opposite the proximal surface, the capture device being operable to draw the distal end of the first wire to a position distal of the distal surface of the occlusion, wherein the capture device comprises a second magnet that is adapted to attract the first magnet.

2. The multiple-wire system of claim 1, wherein the gradually tapered portion tapers from a diameter of about 0.036 cm (0.014 inches) to a diameter of about 0.025 cm (0.010 inches) in a direction from the proximal end of the first inner wire towards the distal end of the first inner wire.

3. The multiple-wire system of claim 1, wherein the gradually tapered portion tapers from a diameter of about 0.036 cm (0.014 inches) to a diameter of about 0.020 cm (0.008 inches) in a direction from the proximal end of the first inner wire towards the distal end of the first inner wire.

4. The multiple-wire system of claim 1, wherein the gradually tapered portion tapers from a diameter of about 0.046 cm (0.018 inches) to a diameter of about 0.025 cm (0.010 inches) in a direction from the proximal end of the first inner wire towards the distal end of the first inner wire.

5. The multiple-wire system of claim 1, wherein the gradually tapered portion tapers from a diameter of about 0.053 cm (0.021 inches) to a diameter of about 0.036 cm (0.014 inches) in a direction from the proximal end of the first inner wire towards the distal end of the inner first wire.

6. The multiple-wire system of claim 1, wherein the capture device further includes a receptor having a distal opening, a proximal end and a channel leading from the distal opening toward the proximal end, wherein the first and second magnets are adapted to draw the distal end of the first wire into the channel.

7. The multiple-wire system of claim 6 wherein the channel of the receptor tapers in a direction from the distal opening toward the proximal end of the receptor.

8. The multiple wire system of claim 1, wherein the capture device comprises:

a second outer wire having a proximal end, a distal end, and a generally cylindrical outer surface, wherein the second outer wire includes an opening adjacent the distal end, an opening adjacent the proximal end, and a central lumen communicating therebetween;

a second middle wire configured for insertion in the blood vessel through the central lumen of the outer wire, the second middle wire having a proximal end, a distal end and a generally cylindrical outer surface, wherein the second middle wire includes an opening adjacent the distal end, an opening adjacent the proximal end, and a central lumen communicating therebetween, wherein the second middle wire is longer than the first outer wire; and a second inner wire having a proximal end and a distal end, and wherein the second inner wire comprises the second magnet.

9. A method of obtaining access through an occlusion in a blood vessel, comprising:

inserting a first wire into the blood vessel to a position where the distal end of the first wire is distal of a proximal surface of the occlusion, wherein the first wire comprises:

a first outer wire having a proximal end, a distal end, and a generally cylindrical outer surface, wherein the first outer wire includes an opening adjacent the distal end, an opening adjacent the proximal end, and a central lumen communicating therebetween;

a first middle wire configured for insertion in the blood vessel through the central lumen of the outer wire, the second wire having a proximal end, a distal end and a generally cylindrical outer surface, wherein the first middle wire includes an opening adjacent the distal end, an opening adjacent the proximal end, and a central lumen communicating therebetween, wherein the first middle wire is longer than the first outer wire; and a first inner wire having a proximal end, distal end and a gradually tapered portion adjacent the distal end, wherein the gradually tapered portion is configured to penetrate and pass through the occlusion, and wherein the gradually tapered portion comprises a first magnet having a diameter no greater than the gradually tapered portion;

inserting a capture device into the blood vessel to a position adjacent the distal end of the first wire; and operating the capture device to draw the distal end of the first wire to a position distal of a distal surface of the occlusion.

10. The method of claim 9, wherein the capture device is inserted into the blood vessel towards a distal surface of the occlusion opposite the proximal surface.

11. The method of claim 9, wherein operating the capture device includes operating a second magnet included on the capture device to attract the first magnet included on the first wire.

* * * * *

UNITED STATES PATENT AND TRADEMARK OFFICE
CERTIFICATE OF CORRECTION

PATENT NO. : 8,545,418 B2
APPLICATION NO. : 12/356446
DATED : October 1, 2013
INVENTOR(S) : Heuser Page 1 of 1

It is certified that error appears in the above-identified patent and that said Letters Patent is hereby corrected as shown below:

Title Page

In column 2 (page 3, item 56) at line 28 (approximately), Under Other Publications, change "Extremeties."" to --Extremities."--.

In column 2 (page 3, item 56) at line 30 (approximately), Under Other Publications, change "Extremeties" to --Extremities--.

In column 2 (page 3, item 56) at line 39 (approximately), Under Other Publications, change "Fistual" to --Fistula--.

In column 2 (page 3, item 56) at line 45 (approximately), Under Other Publications, change "Extremeties."" to --Extremities."--.

In the Specification

In column 3 at line 47, Change "Limited" to --limited--.

In column 6 at line 60, Change "extend" to --extent--.

In column 8 at line 56, Change "e.q.," to --e.g.,--.

In column 8 at line 65, Change "and my" to --and may--.

In column 8 at line 66, Change "campatibility" to --compatibility--.

In column 9 at line 19, Change "Located" to --located--.

In column 9 at line 41, Change "therebeween," to --therebetween,--.

In column 10 at line 28, Change "Wire" to --wire--.

Signed and Sealed this
Seventeenth Day of June, 2014

Michelle K. Lee
*Deputy Director of the United States Patent and Trademark Office*